(12) United States Patent
Parker et al.

(10) Patent No.: US 6,407,286 B1
(45) Date of Patent: Jun. 18, 2002

(54) PROCESS FOR RECOVERING HYDROGEN IN PRODUCING PURE TEREPHTHALIC ACID

(76) Inventors: David Parker, 3 Low Green, Great Ayton, Middlesbrough (GB), TS9 6NN; Fiona Mary Campbell, 2, Manor House Mews, Yarm, Cleveland (GB), TS15 9SG; Andrew Harrison, 23 The Acres, Stokesley (GB), TS9 5QA ( * ) Notice: Subject to any disclaimer, the term of this patent is extended or adjusted under 35 U.S.C. 154(b) by 0 days.

(21) Appl. No.: 09/462,965
(22) PCT Filed: Jul. 17, 1998
(86) PCT No.: PCT/US98/14507
§ 371 (c)(1), (2), (4) Date: Jan. 14, 2000
(87) PCT Pub. No.: WO99/03812
PCT Pub. Date: Jan. 28, 1999

(30) Foreign Application Priority Data

Jul. 16, 1997 (GB) ............................................. 9714907

(51) Int. Cl.$^7$ ................................................ C07C 51/42
(52) U.S. Cl. ........................ 562/486; 562/484; 562/485
(58) Field of Search ................................. 562/486, 485, 562/487

(56) References Cited

U.S. PATENT DOCUMENTS

| 2,833,816 A | 5/1958 | Saffer et al. |
| 3,584,039 A | 6/1971 | Meyer |
| 3,639,465 A | 2/1972 | Olsen et al. |

*Primary Examiner*—Paul J. Killos
(74) *Attorney, Agent, or Firm*—Charles E. Krukiel

(57) ABSTRACT

A method for recovering and recycling excess hydrogen from process vent streams in the production of highly pure terephthalic acid where the production of the pure terephthalic acid comprises catalytically hydrogenating impure terephthalic acid, which typically contains 4-carboxybenzaldehyde (4-CBA), color bodies and other impurities, in aqueous liquid phase solution at elevated temperature and pressure.

2 Claims, 1 Drawing Sheet

PROCESS FOR RECOVERING HYDROGEN IN PRODUCING PURE TEREPHTHALIC ACID

This application claims priority benefit based on GB Provisional Application No. 9714907.4, filed Jul. 16, 1997.

BACKGROUND OF THE INVENTION

The present invention relates to the production of aromatic carboxylic acids, and, more particularly, it relates to a method for recovering and recycling excess hydrogen from process vent streams in the production of highly pure terephthalic acid where the production of the pure terephthalic acid comprises catalytically hydrogenating impure terephthalic acid, which typically contains 4-carboxybenzaldehyde (4-CBA), color bodies and other impurities, in aqueous liquid phase solution at elevated temperature and pressure.

The impure terephthalic acid is dissolved in water in an inert, e.g., nitrogen, atmosphere at a temperature and pressure sufficiently high to provide a solution in liquid phase, and the resulting solution is subjected to hydrogenation in the presence of a Group VIII metal and in the presence of an excess of hydrogen of from 1 to 7 moles over the stoichiometric amount required for the principal reducible impurities, i.e., 4-CBA. The reaction solution is then separated from the catalyst, and pure terephthalic acid (PTA) is isolated from the solution by, typically, a series of crystallization steps in which the solution is cooled by releasing the pressure which, in turn, vaporizes water and dissolved inert gas from the solution and terephthalic acid crystals precipitate. U.S. Pat. No. 3,584,039 reports that vaporized water can be condensed and recycled if desired to the dissolution step. However, pressure reduction also causes excess hydrogen and inert gas to separate from the solution along with other volatile compounds formed by partial decomposition of terephthalic acid and its principal intermediates. Typical decomposition reactions include decarbonylation of 4-CBA to produce $C_6H_5COOH+CO$ and decarbonylation of terephthalic acid to produce $C_6H_5COOH+CO_2$. Carbon monoxide (CO) is a well known poison for hydrogenation catalysts. Depending on the activity level of the hydrogenation catalyst, the decarbonylation reactions (and others) can generate appreciable levels of gaseous impurities in the vented vapor stream, and these impurities, if recycled to the hydrogenation reaction, can be problematic. Consequently, excess hydrogen and other non-condensable components in the vent stream are usually passed through a vent scrubber of some kind and then released to the atmosphere.

SUMMARY OF THE INVENTION

The present invention provides for recovering and recycling excess hydrogen from process vent streams in the production of highly pure terephthalic acid where the production of the pure terephthalic acid comprises catalytically hydrogenating impure terephthalic acid, which typically contains 4-carboxybenzaldehyde (4-CBA), color bodies and other impurities, in aqueous liquid phase solution at elevated temperature and pressure. Commercial processes for producing pure terephthalic acid from an impure terephthalic acid having as impurities 4-carboxybenzaldehyde, color bodies and color forming precursors typically include the steps of:

(1) forming an aqueous solution containing the impure terephthalic acid in an inert atmosphere;

(2) treating the aqueous solution with hydrogen, or a prehumidified hydrogen-containing gas, at a concentration of from 1 to 7 moles above the stoichiometric amount required to reduce the 4-carboxybenzaldehyde present in solution to p-toluic acid in the presence of a Group VIII Noble metal catalyst at elevated temperature and pressure sufficient to maintain the solution in the liquid phase;

(3) separating the treated solution from the catalyst; and (4) crystallizing terephthalic acid from the separated solution in one step, or in a series of graduated steps, by releasing the pressure on the treated solution whereby water and dissolved inert gas vaporize and a vent stream comprising water vapor, inert gas, unreacted excess hydrogen and volatile impurities is formed while non-volatile impurities and their reduction products remain dissolved in the resulting mother liquor. According to the present invention, hydrogen is recovered and recycled to the purification process by:

(a) cooling the vent stream to condense water vapor and condensable impurities;

(b) treating the vent stream to remove uncondensed volatile impurities and recover the hydrogen; and (c) returning the hydrogen to the hydrogenation reaction.

The vent stream, exiting the first crystallizer, or exiting a series of graduated crystallizers, as the case may be, at a temperature in the range of from as low as 210° C. to as high as 280° C. and a pressure of around 2000 kPa absolute (abs.) to 6000 kPa abs., is first passed to a condenser, e.g., a feed preheater, wherein heat is transferred from the vent stream to a process feed or other stream thereby making use of available heat. Condensate and uncondensed vapors then pass to a condensate pot or other suitable means for collecting condensate. The vent stream, now at a temperature in the range of 236° C. and a pressure of around 3200 kPa abs. and comprising steam, unreacted excess hydrogen, inert gas and generally non-condensable components selected from CO, $CO_2$, $CH_4$ and sulfur-containing compounds is let down in pressure to a pressure of around 2000 kPa abs. to insure that the vapors are superheated by about 15° C. above their dew point prior to treatment. The vapors are then treated, i.e., purified, to selectively remove or chemically convert gaseous impurities which otherwise could be harmful if introduced to the hydrogenation reaction, particularly the Group VIII Noble metal catalyst. Although in practice it may not be possible to completely remove all gaseous impurities from the recovered hydrogen stream, the purified stream can be purged to maintain the level of gaseous impurities during operation within acceptable limits. The stream of recovered hydrogen is then compressed to a pressure in the range of 10,000 kPa abs., supplemented with fresh hydrogen, and returned to the hydrogenation reactor.

DETAILED DESCRIPTION

Figure 1:
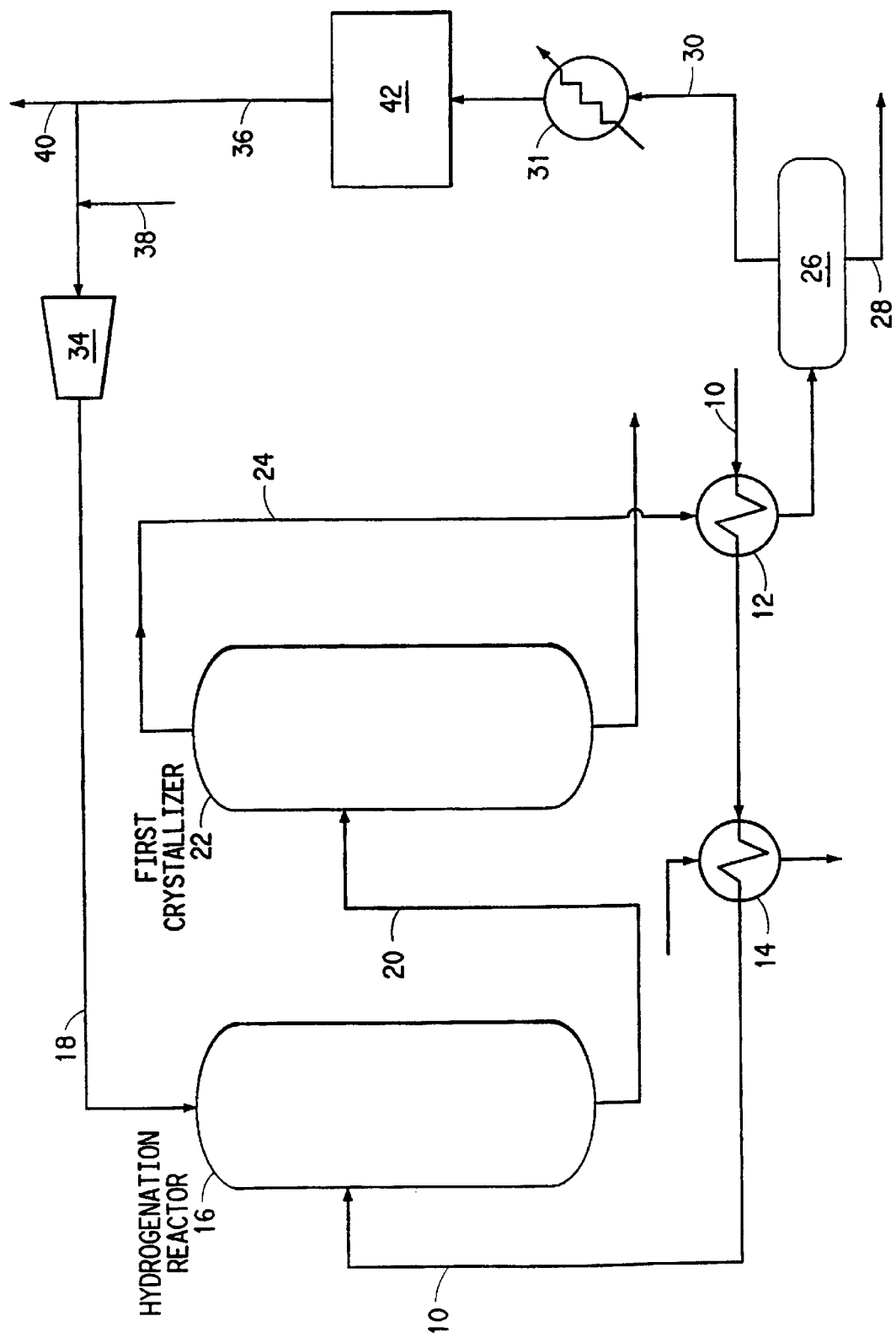
FIG. 1 is a schematic diagram of one embodiment of a hydrogen recovery process according to the invention.

The present invention provides for recovering and recycling excess hydrogen from process vent streams in the production of highly pure, terephthalic acid from impure terephthalic acid, i.e., terephthalic acid produced by the liquid phase air (molecular oxygen) oxidation of paraxylene using a heavy metal and bromine catalyst as described in Saffer et al. U.S. Pat. No. 2,833,816. The process of the present invention may also be used in connection with purification of terephthalic acid produced from other processes based on catalytic liquid phase oxidation of para-dialkylbenzenes with molecular oxygen in the presence of a heavy metal oxidation catalyst, and may be applicable to equivalent reduction processes related to other phthalic acids, such as isophthalic acid and OPA.

The purification of aromatic polycarboxylic acids by catalytic reduction of impurities, such as 4-CBA, using hydrogen or a pre-humidified hydrogen-containing gas is described in Meyer et al. U.S. Pat. No. 3,584,039 and Olsen et al. U.S. Pat. No. 3,639,465. Impure terephthalic acid containing 4-CBA, color bodies and other impurities is dissolved in water in an inert, e.g., nitrogen, atmosphere at a temperature and pressure sufficiently high to provide a solution and to maintain the solution in liquid phase. The resulting solution is subjected to hydrogenation in the presence of a Group VIII metal typically on an inert, e.g. charcoal, support in the presence of hydrogen or a pre-humidified hydrogen-containing gas. Because of its relatively low solubility, terephthalic acid requires either large volumes of water or high temperatures in order to obtain the desired terephthalic acid solution. In practice, the hydrogenation process can be conducted within the range of from 200° C. up to the critical temperature of water (374° C.). Within the preferred temperature range solutions of about 10% by wt. to about 35% by wt. terephthalic acid are used. The temperature of the aqueous solution is typically a few degrees above that required to form a saturated solution. This is to insure that variations in the solution temperature through control or loss of pressure causing vaporization and cooling do not cause premature crystallization. The pressure of the process will then be determined by the sum of the vapor pressure of the aqueous solution plus the pressure of the applied hydrogen reactant. Such hydrogen pressure may be selected to generate the required reductive effect, and is typically in the range of from 0 to 2500 kPa, but may be higher. Most of the impurities in the impure terephthalic acid are occluded in the acid crystals. By dissolving impure terephthalic acid in water, the impurities are then in solution and subject to catalytic hydrogenation treatment.

The hydrogenation process can be practiced using a suitable hydrogenation reactor arranged for intermittent introduction of hydrogen into a bed of catalyst during continuous introduction of the aqueous solution of impure terephthalic acid. The amount of hydrogen used is an excess of the amount required for reduction of the dissolved impurities. Although in practice very little hydrogen is consumed in the hydrogenation, i.e., purification, process, the amount of hydrogen used is in the range of from 1 to 7 moles excess above the stoichiometric amount required for the principle reducible impurities, 4-CBA and the characteristically yellow-colored impurities, while making allowance for other impurities of unknown structure. The nature of the end products of all of these impurities is not known but, by optical density measurement of the terephthalic acid product recovered after catalytic hydrogenation treatment, their absence or lowered concentration can be noted. Severe hydrogenation should be avoided so that conversion of terephthalic acid such other products as cyclohexane, 1,4-dicarboxylic acid and p-toluic acid does not occur.

The hydrogenation catalyst is preferably a Group VIII noble metal selected from platinum and/or palladium supported on adsorbent, high surface area charcoal. Reference may be made to any of the standard texts on hydrogenation or catalysts for materials which are catalytically effective under aqueous phase hydrogenation conditions.

The hydrogen treated aqueous solution can be filtered to remove any suspended solids, such as catalyst support fines and extraneous materials of about 5 microns and larger in size. The purified acid is then recovered from the filtered solution conveniently and preferably via crystallization, or via a series of crystallization steps in which the aqueous solution is cooled by releasing the pressure, which, in turn, vaporizes water and dissolved inert gas from the solution, and thereby causes terephthalic acid crystals to precipitate.

Turning now to the drawing, FIG. 1 is a simplified schematic flow diagram of one embodiment of the invention. It is to be understood that this embodiment is for the purpose of illustration and is not to be regarded as a limitation of the scope of the invention.

Referring to FIG. 1, an aqueous stream which contains crude, i.e., impure, terephthalic acid is introduced via line 10 and a pre-heat train comprising heat exchangers 12 and 14 to hydrogenation reactor 16. Hydrogen is supplied via line 18. The hydrogenation reaction is carried out at a pressure in the range of from 4000 kPa abs. to 20000 kPa abs. and a temperature which can range from 250° C. up to 350° C. in the presence of a Group VIII Noble metal catalyst. The hydrogenated solution is separated from the catalyst and withdrawn from the hydrogenation reactor via line 20 and passed to a series of crystallizers (of which only the first crystallizer 22 is shown). Pressure is released, i.e., let down, in graduated stages whereby water and dissolved inert gas vaporize and a vent stream comprising water vapor, inert gas, unreacted excess hydrogen and volatile impurities is formed while non-volatile impurities remain dissolved in the resulting mother liquor.

The vent stream is passed via line 24 to heat exchanger 12 where it is cooled, typically to a temperature in the range of from 210° C. to 270° C., to condense water vapor and condensable impurities. The condensate is then removed via line 28 from reactor preheater condensate pot 26, and the balance of the vent stream is passed via line 30 to a second heat exchanger 31 for further pressure and temperature reduction and recovery of additional condensable impurities, primarily water vapor. Typically the vent stream passing from reactor preheater condensate pot 26 will be at a pressure in the range of 3200 kPa abs., a temperature in the range of 236° C. and will have the following composition:

| Component | Concentration (%v/v) |
|---|---|
| Hydrogen | 55 |
| $CO_2$ | 1 |
| CO | 0.2 |
| Water Vapor & other constituents | 43.8 |

The pressure of the vent stream is let down to a pressure in the range of 2000 kPa abs. to insure that the vapors are superheated by about 15° C. above their dew point. The vent stream is then treated in a treatment step designated 42 to remove or chemically convert gaseous impurities which otherwise could be harmful to the hydrogenation reaction, primarily CO and $CO_2$. The selection and number of treatment steps will depend on the composition of the vent stream and economic considerations.

Methanation can be employed to convert trace levels of CO in the vent stream to water and $CH_4$ by reacting with $H_2$ as follows:

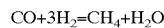

This is an exothermic reaction which takes place over a catalyst of supported nickel oxide. As shown, this type reaction will necessarily consume a small amount of hydrogen.

Alternatively, the impurities in the vent stream can be selectively adsorbed onto a molecular sieve adsorbent according to a process known as pressure swing adsorption. Hydrogen present in the vent stream is not adsorbed due to its high volatility and low polarity.

Another treatment process involves selective oxidation of CO according to the following reaction:

$$CO + \tfrac{1}{2}O_2 = CO_2$$

A competitive reaction takes place simultaneously as follows:

$$H_2 + \tfrac{1}{2}O_2 = H_2O$$

The process uses gaseous oxygen and requires a 0.3% platinum on alumina catalyst.

From reasons of process economics and operability the preferred method for treating the vent stream exiting reactor preheater condensate pot 26 is via a low temperature shift reaction to convert CO to $CO_2$ as follows:

$$H_2O + CO = CO_2 + H_2$$

The vent stream from reactor preheater condensate pot 26 is let down in pressure to 2000 kPa to insure that the gas is above its dew point before entering the "shift converter". The preferred minimum temperature for the gas stream is 15° C. above its dew point to prevent condensation on the catalyst. The relatively large amount of water vapor in the vent stream tends to make the process more feasible than other alternatives with an expected CO conversion of around 99% and a catalyst life of about 3 years. In addition, process makes small but beneficial amounts of hydrogen. A suitable catalyst is a copper oxide, zinc oxide and alumina catalyst, such as "Katalco" 83–3, available from Imperial Chemical Industries.

Following treatment step 42 the now hydrogen rich vapor stream is condensed to a temperature in the range of 50° C. to remove additional remaining water vapor, and the vapor stream can be scrubbed with caustic to remove $CO_2$ to prevent its build-up in the hydrogen recovery and recycle process. Hydrogen recycle stream 36 with fresh hydrogen make-up via line 38 is introduced to the suction side of hydrogen compressor 39 where it is re-compressed to a pressure in the range of 10000 kPa and recycled to the hydrogenation reactor 16 via line 18. To the extent needed, a purge via line 40 can be taken to maintain impurities within tolerable limits.

What is claimed is:

1. In a process for producing pure terephthalic acid from an impure terephthalic acid having as impurities 4-carboxybenzaldehyde, color bodies and color forming precursors which comprises:

(1) forming an aqueous solution containing the impure terephthalic acid in an inert atmosphere;

(2) treating the aqueous solution with hydrogen at a concentration of from 1 to 7 moles over the stoichiometric amount required to reduce the 4-carboxybenzaldehyde present in solution to p-toluic acid in the presence of a Group VIII Noble metal catalyst at elevated temperature and pressure sufficient to maintain the solution in the liquid phase;

(3) separating the treated solution from the catalyst;

(4) crystallizing terephthalic acid from the separated solution by releasing the pressure on the treated solution in one step, or in a series of graduated steps, whereby water and dissolved inert gas vaporize and a vent stream comprising water vapor, inert gas, excess hydrogen and volatile impurities selected from CO, $CO_2$, and $CH_4$ is formed while non-volatile impurities and their reduction products remain dissolved in the resulting mother liquor; and (5) cooling the vent stream to condense water vapor and condensable impurities; the improvement comprising:

(a) treating the vent stream to remove or chemically convert uncondensed volatile impurities to inert components and recover the hydrogen; and (b) returning the hydrogen to the hydrogenation reaction.

2. The process of claim 1 which includes the additional steps of treating the vent stream in step (a) in the presence of a copper oxide, zinc oxide and alumina catalyst to chemically convert CO to $CO_2$, and removing the $CO_2$ from the vent stream by caustic scrubbing.

\* \* \* \* \*